United States Patent [19]

Hilti et al.

[11] 4,384,025
[45] May 17, 1983

[54] METALLICALLY CONDUCTING 5,6,11,12-TETRATHIOTETRACENE-IODINE CHARGE-TRANSFER COMPLEX AND PROCESSES FOR THE PRODUCTION THEREOF

[75] Inventors: Bruno Hilti, Basel; Carl W. Mayer, Riehen, both of Switzerland

[73] Assignee: Ciba-Geigy Corporation, Ardsley, N.Y.

[21] Appl. No.: 721,268

[22] Filed: Sep. 8, 1976

[30] Foreign Application Priority Data

Sep. 19, 1975 [CH] Switzerland .................. 12230/75

[51] Int. Cl.$^3$ .................. C07D 495/06; B32B 9/04; H01B 1/00
[52] U.S. Cl. .................. 428/411; 252/500; 260/239 R; 549/31
[58] Field of Search .................. 260/327 C, 239 R; 428/411; 252/500; 549/31

[56] References Cited

U.S. PATENT DOCUMENTS 3,634,336  1/1972  Perez-Albuerne .............. 252/519
4,046,950  9/1977  Isett .................. 252/500

OTHER PUBLICATIONS

Isett et al., Solid State Communications, vol. 21, (1977), pp. 433-435.
Isett, Research Disclosure, Aug. 1976, 14832, pp. 21 and 22.
Perez-Albuerne et al., J. Chem. Physics, 55, 1547-1554, (1971).

Primary Examiner—Benjamin R. Padgett
Attorney, Agent, or Firm—Luther A. R. Hall

[57] ABSTRACT

A novel metallically conducting charge-transfer complex derived from 5,6,11,12-tetrathiotetracene and iodine is described. This complex is preferably produced by reacting 5,6,11,12-tetrathiotetracene and iodine together in the gas phase in an inert-gas atmosphere. The novel complex is characterized by a very high electrical conductivity, and it can be used, for example, as an organic conductor element.

12 Claims, 2 Drawing Figures

METALLICALLY CONDUCTING 5,6,11,12-TETRATHIOTETRACENE-IODINE CHARGE-TRANSFER COMPLEX AND PROCESSES FOR THE PRODUCTION THEREOF

The invention relates to a novel metallically conducting charge-transfer complex derived from 5,6,11,12-tetrathiotetracene (TTT) and iodine, as well as to processes for producing this complex.

Tetrathiotetracene-halogen complexes, inter alia tetrathiotetracene-iodine complexes, having semiconductor properties are described in the French Patent Specification No. 2,058,353. Films from a tetrathiotetracene-iodine complex, not stoichiometrically more precisely specified, have according to this patent specification a surface resistance of $2.0 \times 10^7$ ohm/cm². These tetrathiotetracene-halogen complexes are produced by reaction of soluble derivatives of tetrathiotetracene, e.g. tetrathiotetracene-acetate, with inorganic salts, e.g. alkali metal halides, such as NaBr, in solution.

E. A. Perez-Albuerne et al. [The J. Chemical Physics, 55, 1547-1554 (1971)] describe microcrystalline tetrathiotetracene-iodine complexes that are produced in an analogous manner by reaction of tetrathiotetracene-acetate with NaI or KI. Even with the use in this case of an excess of NaI or KI, exclusively tetrathiotetracene-iodine complexes having a ratio of tetrathiotetracene to iodine of 1:0.9–1.0 are obtained. These microcrystalline complexes likewise have semiconductor properties and have a resistivity of 0.71 ohm-cm at room temperature. According to this publication, deviations from the 1:1 ratio of tetrathiotetracene to iodine do not greatly affect the conductivity level of the corresponding complexes.

Finally, the U.S. Pat. No. 3,403,165 discloses tetrathiotetracene ion-radical salts derived from tetrathiotetracene and tetracyanoethylene or an o- or p-benzoquinone containing at least two electronegative substituents, such as o-chloroanil, o-bromoanil, o-iodoanil and the corresponding para compounds. These complexes likewise have semiconductor properties.

The present invention provides a novel 5,6,11,12-tetrathiotetracene-iodine complex of the formula

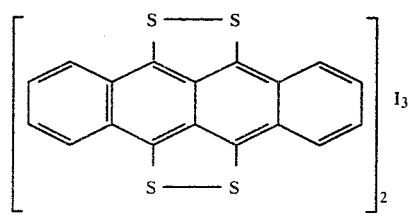

having metallically conducting properties. This complex can be produced in a simple manner by reacting tetrathiotetracene with $I_2$ in a molar ratio of 4:3. From a chemical point of view, the reaction occurring is a redox reaction, i.e. a partial oxidation of the 5,6,11,12-tetrathiotetracene by the iodine.

In the complex according to the invention, the tetrathiotetracene is the electron donor and the iodine the electron acceptor. The complex according to the invention has a very high electrical conductivity [$\sigma$ at room temperature up to 8000 ohm$^{-1}$ cm$^{-1}$, measured along the preferred direction of growth (needle axis)]. Its temperature dependence has metallic character, i.e. the electrical conductivity increases from room temperature (20°–25° C.) to about 35° K. (−238.15° C.). The complex according to the invention is hence characterised not only in that it has the highest room-temperature conductivity hitherto known for organic compounds but also in that it constitutes the first metallically organic charge-transfer complex with iodine.

The complex according to the invention contains the space group $C_{mca}$. The lengths of the axes of the elementary cell are:

$a = 18.377 \text{ Å}$
$b = 4.945 \text{ Å}$ and $c = 18.484 \text{ Å}$.

Both the tetrathiotetracene molecules and the iodine form separated columns in the direction of the axis (needle axis). The iodine columns are uncorrelated with one another. Their periodicity is 9.9 Å, i.e. twice the b-axis unit.

The complex according to the invention can be in the form of a microcrystalline powder and particularly in the form of single crystals.

The complex according to the invention can be obtained by various methods. The method of producing the TTT-iodine complex according to the invention from the gas phase (sublimation) has proved particularly advantageous. In this case the tetrathiotetracene is reacted with the iodine advantageously in an inert-gas atmosphere, preferably in an open system. The reaction in the gas phase however can be performed also in a closed system with an inert-gas atmosphere. It is possible by this process to obtain very pure crystals containing practically no impurities, such as solvent molecules. The crystals obtained by sublimation are moreover characterised by optically faultless surfaces and by a particularly high electrical conductivity.

The reaction in the gas phase can be performed, for example, by passing iodine vapour by means of an inert carrier gas over the 5,6,11,12-tetrathiotetracene heated to about 270° C. The $(TTT)_2I_3$ crystals then grow on the reactor walls and/or on a substrate optionally arranged in the reactor.

In a particularly preferred embodiment according to the invention, both reactants are reacted in the vapour form. The reactants are advantageously introduced by means of inert gases into a reaction zone in which there is a temperature gradient.

A brief description of FIGS. 1 and 2:

Figure 1:
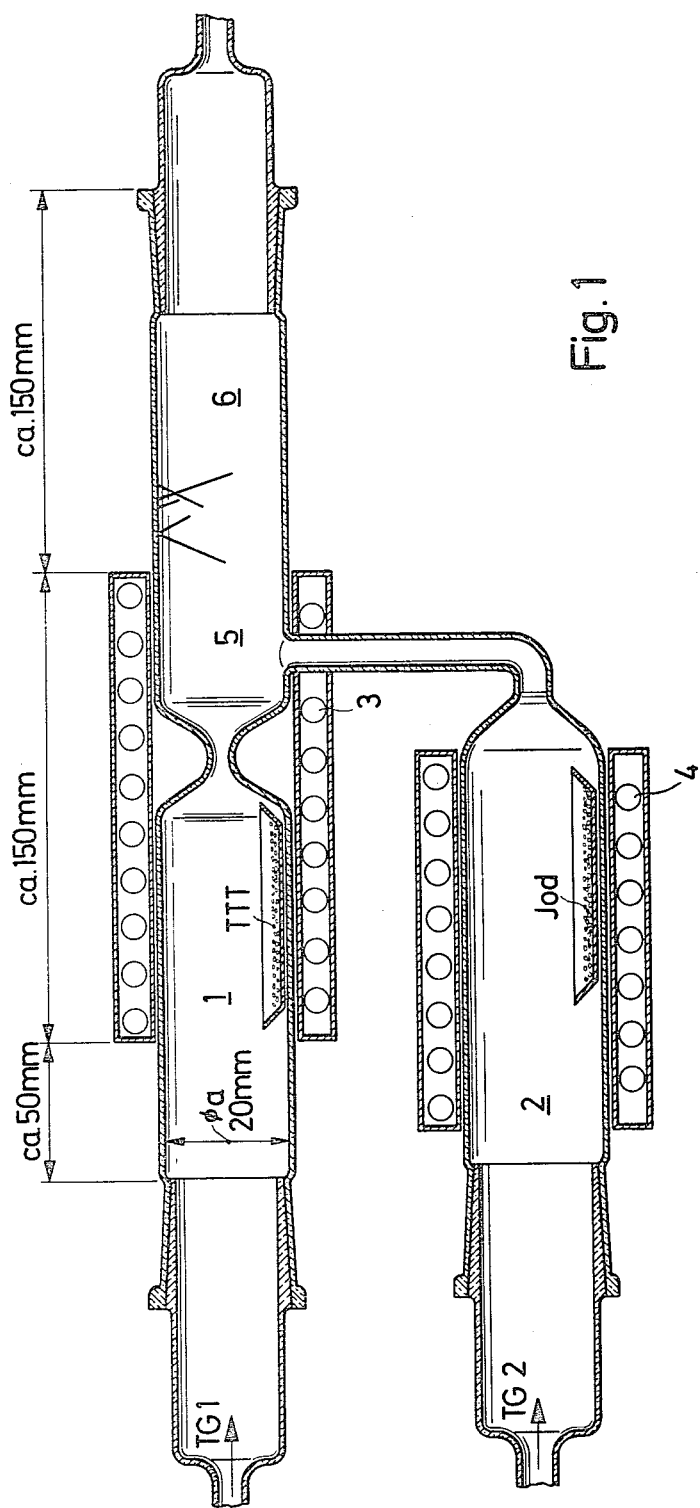
FIG. 1 shows an experimental arrangement.

FIG. 1 illustrates an experimental arrangement that is particularly suitable for the reaction in the gas phase. The 5,6,11,12-tetrathiotetracene and the iodine are vaporised in separate chambers (1,2) provided with heating elements (3) and with a thermostat (4), and the vapours are then introduced by means of the carrier gases TG 1 (for TTT) and TG 2 (for the iodine) into the reaction chamber (5). The crystals of the complex according to the invention grow at the colder end of the reaction chamber (6) either on the walls of the reactor or on a substrate arranged in the reaction chamber. The reaction vessels can be made, e.g., of Pyrex glass, preferably however of quartz.

The carrier gases employed are advantageously inert gases of high purity, such as argon, nitrogen, helium and xenon. TG 1 and TG 2 in the experimental arrangement according to FIG. 1 can be different or identical. It is preferable to use high-purity argon both for the 5,6,11,12-tetrathiotetracene and for the iodine.

The substrate on which the crystals form can be, for example, aluminium oxide or preferably quartz, in any desired form, e.g. in the form of rods, tubes and so forth.

Figure 2:
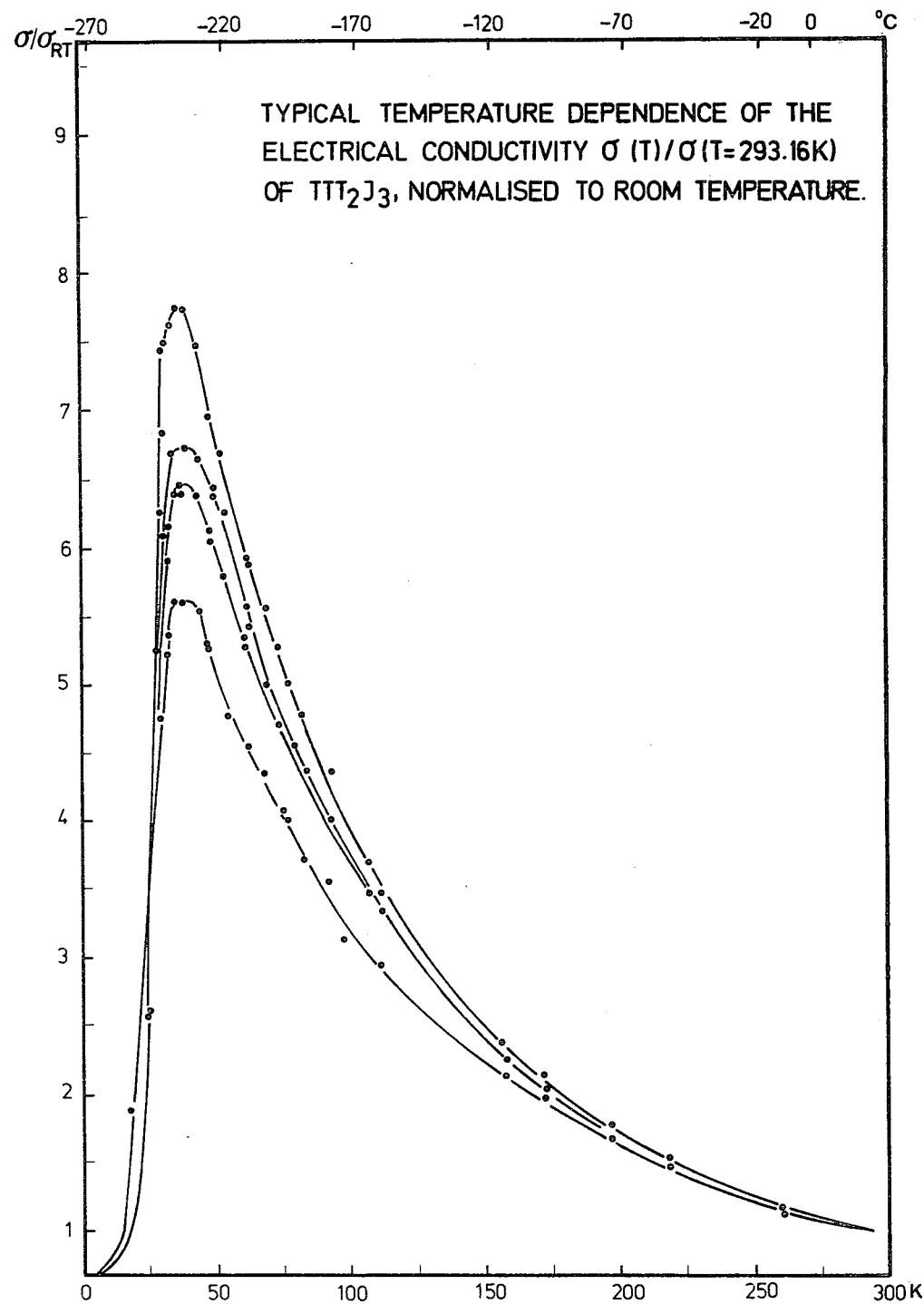
FIG. 2 is a relative graphic representation.

The reaction temperatures in the gas-phase reaction are preferably between about 230° C. and 350° C. The reactants are used in at least stoichiometric amounts. Preferably, however, an excess of iodine is used, advantageously an approximately 10- to 100-fold molar excess. The crystals obtained by sublimation can easily be removed from the reaction zone and from the substrate. FIG. 2 shows the temperature dependence of the electrical conductivity of the complex according to the invention.

The complex according to the invention can be produced also by the solvent process, i.e. by reaction of 5,6,11,12-tetrathiotetracene with iodine in the presence of an inert organic solvent. Suitable inert organic solvents are, in particular, high-boiling, halogenated, especially chlorinated, aromatic hydrocarbons, such as 1,2,3-trichlorobenzene, 1,2,4-trichlorobenzene, chlorinated naphthalenes and o-dichlorobenzene; and also polar solvents such as N,N-dialkylamides of monocarboxylic acids having 1-4 carbon atoms in the acid moiety, e.g. N,N-dimethylformamide and N,N-dimethylacetamide, or dialkylsulphoxides, e.g. dimethylsulphoxide. The preferred solvent is 1,2,4-trichlorobenzene.

Where the reaction occurs in solution, the reaction temperatures are as a rule between about 150° and 220° C. The tetrathiotetracene and the iodine are preferably used in a stoichiometrical amount. The formation of the complex salts is generally completed within a few minutes.

The precipitated complex salt can be isolated and purified in the customary manner; for example by filtration and repeated washing with a suitable organic solvent, such as benzene. Depending on the choice of crystallisation conditions, the tetrathiotetracene-iodine complex according to the invention is obtained either as a microcrystalline powder having a golden lustre, or as single crystals in the form of needles having a metallically golden lustre.

Finally, the complex according to the invention can be obtained also by diffusion of iodine from the gas phase, or from a suitable carrier solution, into a solution of 5,6,11,12-tetrathiotetracene, e.g. in N,N-dimethylacetamide.

It is also possible to coat inorganic or organic substrates directly with the complex according to the invention by vaporising the 5,6,11,12-tetrathiotetracene and the iodine onto a suitable substrate, e.g. quartz, mica or plastics sheets.

By virtue of the metallic-electric and metallic-optical properties, particularly with respect to the very high electrical conductivity with metallic temperature behaviour, the tetrathiotetracene-iodine complex according to the invention is suitable in particular for use as an organic conductor element having a low specific weight (specific weight about 2 g/cm³), for which purpose it is preferably used in the form of single crystals. Owing to the marked temperature dependence of the conductivity over a wide temperature range, the single crystals according to the invention are also excellently suitable for producing thermistors.

The crystals of the complex according to the invention exhibit a pronounced anistropy of the optical properties and can therefore be used, e.g., as polariser materials.

Further fields of application for the complex according to the invention, especially when in the form of microcrystalline powders, are: as additive for the obtainment of specific electrical properties and enhanced heat conductivity in plastics sheets; as grey-green, electrically conducting pigment difficultly soluble in conventional organic solvents; and as catalyst, e.g. for radical polymerisations, such as those of styrene.

EXAMPLE

The test is carried out in an arrangement according to FIG. 1. In chamber 1, 4 mg of 5,6,11,12-tetrathiotetracene (0.0114 mmole) is heated in a quartz boat by the heating element 3 to 290° C. The formed tetrathiotetracene vapour is fed by means of the carrier gas TG 1 [argon 99.9997% vpm (volume per million); rate of flow 7 liters/hour] into the reaction zone 5. 50 mg of iodine (0.2 mmole) ("Suprapur", Merck, Darmstadt, West Germany) in a quartz boat is introduced into chamber 2. The iodine vapour forming at 20° C. is passed by means of the carrier gas TG 2 [argon 99.9997 vpm; rate of flow 5 liters/hour] through the second tube, leading into the reaction zone, into the reaction chamber 5. The temperature of the quartz boat containing the iodine is maintained at 20° C. by means of the thermostat 4. After a reaction time of 7 hours, crystals having a pronounced metallically golden lustre have formed on the tube wall 6 adjacent to the reaction zone 5. Dimensions of the crystals: approx. 2 cm×0.5–30μ×1–200μ.

Analysis for $C_{36}H_{16}S_8I_3$ (molecular weight 1085.70): Calculated: C 39.83%; H 1.49%; I 35.07%. Found: C 39.7%; H 1.9%; I 35.1%. Conductivity of the crystals (measured along the needle axis) at room temperature (20°–25° C.): up to 8000 ohm$^{-1}$cm$^{-1}$. On cooling to 35° K. (= −238.15° C.) by means of liquid helium, the conductivity increases by the factor 5.5 (see FIG. 2).

We claim:

1. Metallically conducting 5,6,11,12-tetrathiotetracene-iodine complex of the formula

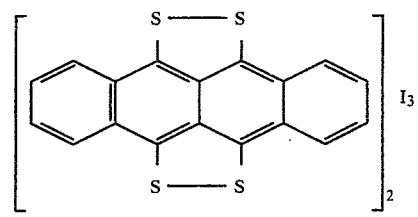

2. 5,6,11,12-Tetrathiotetracene-iodine complex according to claim 1, which complex is in the form of single crystals or of microcrystalline powder.

3. Process for producing a metallically conducting tetrathiotetracene-iodine complex of the formula according to claim 1, in which process 5,6,11,12-tetrathiotetracene and $I_2$ are reacted together in a molar ratio of 4:3.

4. Process according to claim 3, wherein 5,6,11,12-tetrathiotetracene and iodine are reacted together in the gas phase in an inert-gas atmosphere.

5. Process according to claim 4, wherein the reaction in the gas phase is performed at a temperature of between about 230° and 350° C.

6. The composition of matter $(tetrathiotetracene_2)^+(I_3)^-$.

7. An element comprising a support having thereon a layer containing the composition of matter according to claim 6.

8. An element according to claim 7 wherein said layer is in the form of a binderless thin film.

9. A process for preparing (tetrathiotetracene$_2$)$^+$(I$_3$)$^-$ comprising the steps of
   1. forming a vapor of tetrathiotetracene;
   2. forming a vapor of iodine; and
   3. reacting the tetrathiotetracene vapor with the iodine vapor at a temperature of about 230° C. to 350° C. in a substantially inert atmosphere.

10. A process according to claim 9 wherein said inert atmosphere comprises an inert gas selected from the group consisting of argon, nitrogen, helium and xenon.

11. A process according to claim 9 wherein the reaction is carried out in a tube furnace.

12. A process according to claim 9 wherein the reaction is carried out in a flow reactor.

* * * * *